United States Patent
Fox, III (10) Patent No.: US 10,864,291 B2
(45) Date of Patent: Dec. 15, 2020

(54) PROCESS AND APPARATUS FOR CLEANING, DISINFECTION, STERILIZATION, OR COMBINATIONS THEREOF

(71) Applicant: Ethicon, Inc., Somerville, NJ (US)

(72) Inventor: Morris Fuller Fox, III, Tustin, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 149 days.

(21) Appl. No.: 15/854,369

(22) Filed: Dec. 26, 2017

(65) Prior Publication Data

US 2019/0192711 A1    Jun. 27, 2019

(51) Int. Cl.
*A61L 2/24* (2006.01)
*A61L 2/20* (2006.01)
(Continued)

(52) U.S. Cl.
CPC ............... *A61L 2/24* (2013.01); *A61B 90/70* (2016.02); *A61L 2/14* (2013.01); *A61L 2/208* (2013.01);
(Continued)

(58) Field of Classification Search
CPC ..... A61L 2/14; A61L 2/24; A61L 2/28; A61L 2/208; A61B 90/70
See application file for complete search history.

(56) References Cited

U.S. PATENT DOCUMENTS

| 5,042,367 A | 8/1991 | Hopkins |
| 5,405,231 A | 4/1995 | Kronberg |

(Continued)

FOREIGN PATENT DOCUMENTS

| CA | 2553806 A1 | 8/2005 |
| CA | 2593544 C | 9/2014 |

(Continued)

OTHER PUBLICATIONS

Glove Boxes and Air Lock Chambers—Cleanroom Synergy, Cleanroom Synergy, LLC, accessed at http://cleanroomsynergy.com/products/glove-boxes-air-lock-chambers/, Nov. 15, 2017, 11 pages.
(Continued)

*Primary Examiner* — Sean E Conley
(74) *Attorney, Agent, or Firm* — K&L Gates LLP (57) ABSTRACT

Apparatus and methods are provided for cleaning, disinfecting, and/or sterilizing a device. More specifically, a first treatment chamber can be configured to conduct a first treatment stage therein at a first pressure, a first temperature, and a first sterilant concentration. A first passage can be operatively connected to the first treatment chamber and a second treatment chamber can be operatively connected to the first passage and in communication with the first chamber via the first passage. The second chamber can be configured to conduct a second treatment stage therein at a second pressure, a second temperature, and a second sterilant concentration. An object can be treated in the first treatment chamber and moved to the second treatment chamber via the first passage to be treated in the second treatment chamber.

21 Claims, 4 Drawing Sheets

(51) Int. Cl.
*A61L 2/14* (2006.01)
*A61B 90/70* (2016.01)
*A61L 2/28* (2006.01)

(52) U.S. Cl.
CPC .......... *A61L 2/28* (2013.01); *A61L 2202/122* (2013.01); *A61L 2202/123* (2013.01); *A61L 2202/14* (2013.01); *A61L 2202/24* (2013.01)

(56) References Cited

U.S. PATENT DOCUMENTS

| | | | |
|---|---|---|---|
| 6,066,294 | A | 5/2000 | Lin et al. |
| 6,936,434 | B2 | 8/2005 | McDonnell et al. |
| 6,841,124 | B2 | 11/2005 | Chien et al. |
| 7,357,896 | B2 | 4/2008 | Morrison |
| 7,544,325 | B2 | 6/2009 | Hill et al. |
| 8,641,985 | B2 | 2/2014 | Shilderman et al. |
| 8,808,631 | B2 | 8/2014 | Hill et al. |
| 2003/0015505 | A1 | 1/2003 | Yu et al. |
| 2003/0129111 | A1* | 7/2003 | Miller ............... A61L 2/202 422/292 |
| 2003/0132227 | A1* | 7/2003 | Geisler ............... B07C 1/00 219/700 |
| 2006/0257287 | A1* | 11/2006 | Call ............... B01D 45/04 422/83 |
| 2007/0062911 | A1 | 3/2007 | Siebels |
| 2008/0032059 | A1 | 2/2008 | Zimmerer et al. |
| 2009/0047173 | A1* | 2/2009 | Mielnik ............... A61L 2/206 422/28 |
| 2011/0008207 | A1 | 1/2011 | Arai et al. |

FOREIGN PATENT DOCUMENTS

| | | |
|---|---|---|
| CN | 101810871 A | 8/2010 |
| DE | 4408301 A1 | 9/1994 |
| EP | 1704873 B1 | 12/2010 |
| WO | WO 2008/116921 A1 | 10/2008 |

OTHER PUBLICATIONS

Mace, Bob, "Everything You Need to Know About Rotary Airlock Valves", www.iac-intl.com, May 2016, 15 pages.

Benchtop Stainless Steel Vacuum Glove Box (31"×26"—28") with Airlock and Vacuum Flange & Gauge, accessed at http://www.batteryspace.com/Benchtop-Stainless-Steel-Vacuum-Glove-Box-31-x-26-x-28.aspx on Nov. 15, 2017, 3 pages.

* cited by examiner

PROCESS AND APPARATUS FOR CLEANING, DISINFECTION, STERILIZATION, OR COMBINATIONS THEREOF

FIELD OF THE INVENTION

The present disclosure relates to apparatus and methods for cleaning, disinfecting, and/or sterilizing a device.

BACKGROUND

Various medical devices are employed for procedures in the medical field. These devices are as varied as the treatments themselves. As such, proper care of these devices is critical for the proper corresponding treatment of the patient.

Prior to use on a patient, the devices may be treated by various treatment processes (e.g., a cleaning process, a disinfecting process, a sterilizing process, and the like) utilizing heat, such as provided by steam, and/or a chemical, such as hydrogen peroxide, and/or irradiation, such as ultra-violet light, and/or pressure. The process used for treatment may be chosen base on a device parameter such as, type, quantity, geometry, texture, material composition, soil level, and/or bioburden. For example, a medical device which contains a lumen may be harder to clean and require a harsher treatment process than a medical device without a lumen. Whereas a medical device with a sensitive component may degrade upon exposure to the harsher treatment process. Thus, the medical device with the sensitive component may be suited for a milder treatment processes.

When multiple dissimilar devices are treated in a mixed batch treatment process, all devices in the batch are exposed to the same treatment process. The treatment process for the batch may be chosen based on the most difficult to treat device in the batch to ensure the appropriate level of treatment is achieved. As a result, less difficult to treat devices in the batch may be over treated and/or degraded by the treatment process.

SUMMARY

In one aspect, the present disclosure provides an apparatus for treatment. The apparatus comprises a first treatment chamber and a second treatment chamber operatively connected to a passage. The first and second chambers are in communication via the passage. The first treatment chamber is configured to conduct a first treatment stage therein at a first pressure, a first temperature, and a first sterilant concentration. The second treatment chamber is configured to conduct a second treatment stage therein at a second pressure, a second temperature, and a second sterilant concentration.

In another aspect, the present disclosure provides an apparatus for treatment. The apparatus comprises a first treatment chamber and a second treatment chamber operatively connected to a passage. The first and second chambers are in communication via the passage. The first treatment chamber is configured to conduct a first treatment stage therein at a first pressure, a first temperature, and a first sterilant concentration. The second treatment chamber is configured to conduct a second treatment stage therein at a second pressure, a second temperature, and a second sterilant concentration that is different from at least one of the first pressure, the first temperature, and the first sterilant concentration, respectively. A shuttle system is provided in communication with the second chamber. The shuttle system is configured to transport an object between the first chamber and the second chamber via the first passage. A programmable hardware device is configured to control a parameter in at least one of the first treatment stage and the second treatment stage. The parameter is selected from the group consisting of the first pressure, the first temperature, the first sterilant concentration, the second pressure, the second temperature, the second sterilant concentration, a time the object spends in at least one of the first chamber and the second chamber, and combinations thereof.

In another aspect, a method for treating an object is provided. The object is placed into the first treatment chamber and treated in a first treatment stage at a first pressure, a first temperature, and a first sterilant concentration. The object is moved from the first chamber into a second chamber via a passage and treated in a second treatment stage at a second pressure, a second temperature, and a first sterilant concentration.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification such that amending to expressly recite any such sub-ranges would comply with the requirements of 35 U.S.C. § 112 and 35 U.S.C. § 132(a).

Various medical devices are employed for procedures in the medical field. For example, when the medical device is an endoscope, these devices are commonly employed to examine the interior of a hollow organ or cavity of the body. Accordingly, each device can have unique features and/or materials to achieve a specific purpose or to be employed in a specific area of the body. However, a mixed batch treatment process exposes various devices to the same treatment process. The treatment process can be chosen to be harsh enough to achieve a sufficient level of sterilization for all devices while limiting degradation of a more sensitive device. However, if the treatment process is too harsh, the sensitive device may degrade. Separating the devices into multiple batches with separate processes based on the type of device(s) in the batch (e.g., a high bio-burdened devices, a sensitive device, etc.) can maximize the level of sterilization for the devices while minimizing degradation. However, running the separate processes sequentially can increase the amount of time required to achieve a sufficient level of sterilization for the devices. Additionally, running each process concurrently in separate treatment apparatuses can increase the cost and footprint of the equipment needed for the processes.

Concurrently operating treatment processes in the same treatment apparatus can minimize the cost and footprint of the treatment apparatus while maximizing the level of sterilization and minimizing degradation. Thus, an apparatus and a method are provided for treatment. More specifically, a first treatment chamber can be configured to conduct a first treatment stage therein at a first pressure, a first temperature, and a first sterilant concentration. A first passage can be operatively connected to the first treatment chamber and a second treatment chamber can be operatively connected to the first passage and in communication with the first chamber via the first passage. The second chamber can be configured to conduct a second treatment stage therein at a second pressure, a second temperature, and a second sterilant concentration. An object can be treated in the first treatment chamber and moved to the second treatment chamber via the first passage to be treated in the second treatment chamber.

A treatment process may be a cleaning process, a disinfecting process, a sterilization process, the like, and combinations thereof. As known in the art, a cleaning process may be a process which reduces and/or eliminates a dirt, a dust, a particle and the like. As known in the art, a disinfecting process may be a type of a cleaning process which reduces and/or eliminates bacteria and/or other forms of living organisms. As known in the art, a sterilization process may be a type of disinfecting process which reduces and/or eliminates bacteria and/or other forms of living organisms that results in a sterilized object being "substantially free" from bacteria and/or other forms of living organisms. As used herein "substantially free" is meant to mean that the object is at least 90% free of contamination, in some examples at least 95% free, in other examples at least 99% free, in other examples at least 99.9% free, in other examples at least 99.99% free, in some examples at least 99.999% free, and in other examples at least 99.9999% free. The sterilization process may include, for example, heat, a sterilant, irradiation, pressure, and combinations thereof. The sterilant may be a chemical capable of sterilization, such as, for example, hydrogen peroxide, ethylene oxide, nitrogen oxide, ozone, glutaraldehyde, formaldehyde, peracetic acid, chlorine, iodine, sodium hydroxide, and combinations thereof.

In one example, a first treatment process may subject the object to high temperature conditions of at least 121 degrees centigrade, under a pressure elevated over atmospheric pressure, for a period of time of at least 3 minutes. In one example, a second treatment process may subject the object to high temperature conditions of at least 160 degrees centigrade, under a pressure substantially similar to atmospheric pressure, for a period of at least 2 hours. In one example, a third treatment process may subject the object to chemical treatment at a temperature of at least 20 degrees centigrade, for example between 20-75 degrees centigrade, under a pressure less than atmospheric pressure, such as 1 to 750 torr, for example, 10 to 100 torr. The third treatment process may be conducted with a sterilant present in the chamber, such as hydrogen peroxide, at a concentration of at least 1% by weight, in other examples of at least 10% by weight, and in other examples of at least 30% by weight, for a period of at least 5 minutes, and in other examples for a time period of at least 10 minutes, and in other examples for a time period between 20-120 minutes. As known in the art, the hydrogen peroxide can be used as a liquid and/or a vapor. Accordingly, the parameters of the treatment process are for illustration purposes only and should not be considered limiting.

The treatment process may be conducted in a single stage or in multiple stages. For example, the treatment process may include an intake stage, an exposure stage, and an exit stage. The intake stage may include establishing a treatment condition which may include, for example, a temperature, a pressure, and/or a sterilant concentration which facilitates the treatment process. In one example, the intake stage may include preconditioning of the object to be treated. The exposure stage can maintain the treatment condition and/or adjust the treatment condition. The exit stage can remove the treatment condition. Each stage may have an associated dwell time and/or ramp to/from the treatment condition. Accordingly, the quantity of stages within the treatment process is for illustration purposes only and should not be considered limiting.

In one example, the intake stage may include achieving a set of first conditions including an elevated temperature (e.g., greater than 20 degrees centigrade), a pressure lower than atmospheric pressure, and a first concentration of sterilant (e.g., greater than 1% hydrogen peroxide vapor by weight). The intake stage may include a ramp time to achieve the first conditions from initial conditions, the initial conditions which may be, for example, 20 degrees centigrade, atmospheric pressure, and a minimal concentration of sterilant, such as less than 0.1% hydrogen peroxide by weight.

In one example, following the intake stage, the exposure stage can maintain the first conditions for a dwell time. In one example, the exposure stage treats the load wherein most of the lethality (e.g., degree of death of bacteria and/or other forms of living organisms) can be accumulated by the object. In one example, for example, following the exposure stage, the exit stage may achieve exit conditions which can be, for example, returning the object to a set of conditions similar to or the same as the initial conditions. Accordingly, treatment of the object can include exposing the object to the intake, exposure, and exit stages of the treatment process.

Figure 1:
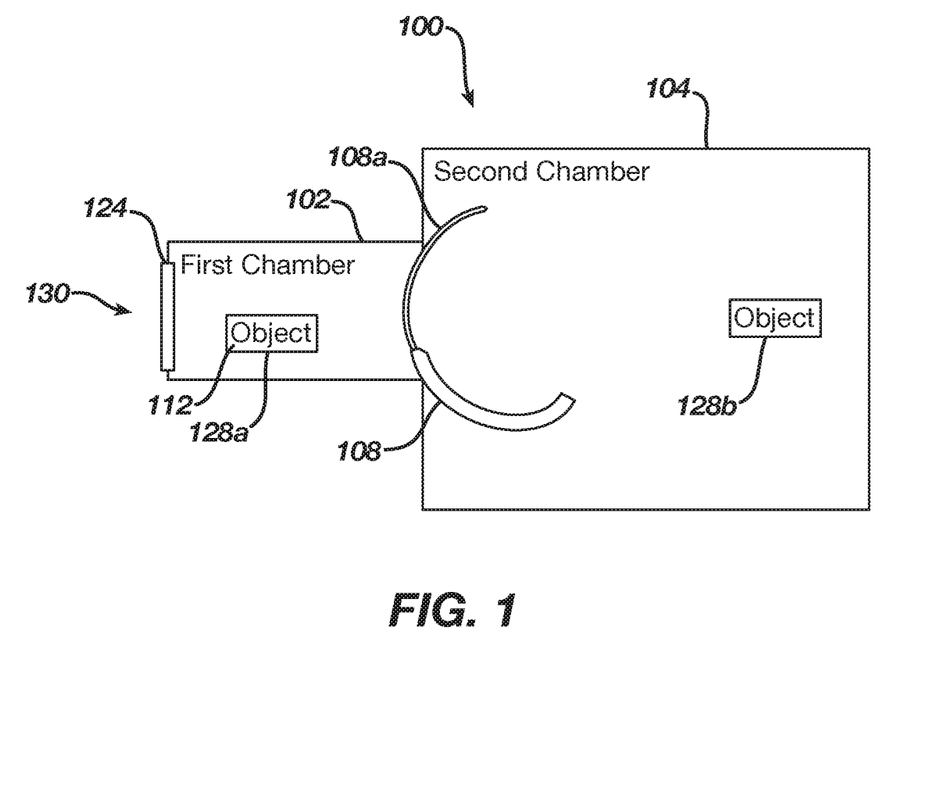
FIG. 1 is a block diagram illustrating an apparatus for treating an object.

FIG. 1 illustrates an apparatus 100 for treating an object 112. The object 112 can be a medical device such as, for example, an endoscope, forceps, a clamp, a retractor, a cutter, a dilator, a tube, a fitting, a stapler, a needle, a drill, a scope, a probe, and combinations thereof. As shown, a first chamber 102 is configured with a first opening 124. The first opening 124 can be configured to receive an object 112 that is, or will be treated. The first opening 124 can have at least two states of communication, including a first state (e.g., an open state) which enables transport of the object 112 into/out of the first chamber 112 and a second state (e.g., a closed state, a sealed state, etc.) which limits transport of the object 112 into/out of the first chamber 112 for a first stage of treatment. In one example, the first opening 124 can be sealable opening such as a door. As described in more detail below, in one example, the first chamber 102 can be an airlock.

The first chamber 102 can be configured to support the treatment process such as conducting a first treatment stage therein at a first pressure, a first temperature, and/or a first sterilant concentration. The first treatment stage can be any portion of the treatment process, such as, for example, the intake stage, the exposure stage, the exit stage, a subset thereof, and combinations thereof. The object 112 can be subjected to the first treatment stage including subjecting the object 112 to the first pressure, the first temperature, and/or the first sterilant concentration. In one example, during the first treatment stage the first opening 124 is in the second state. In one example, the object 112 is in a first position 128a within the first chamber 102 during the first treatment stage.

As shown, the first chamber 102 can be operatively coupled to a second chamber 104. A first passage 108 may be configured to control communication between the first and second chambers, 102 and 104 respectively. For example, in one example, the first passage 108 has at least two states of communication, including a first state (e.g., an open state) which enables the first and second chambers, 102 and 104, respectively, to exchange at least one of: a fluid, heat, and pressure and a second state (e.g., a closed state, a sealed state, etc.) which enables separation of the first and second chambers, 102 and 104, respectively. In one example, in order to change states, the first passage 108 is moveable along a path 108a from a first location to a second location. The first location corresponds to the first state of the first passage 108 wherein a movement of the object 112 between the first and second chambers, 102 and 104 respectively, is not, or can be minimally, impeded by the first passage 108. The second location corresponds to the second state of the first passage 108 wherein the first passage 108 creates a seal between the first and second chambers, 102 and 104, respectively, and can limit movement of the object 112 between the first and second chamber, 102 and 104, respectively.

In one example, the first chamber 102 can be an airlock. The airlock can permit passage of the object 112 while minimizing a change in pressure, a change in temperature, a change in sterilant concentration, and/or an exchange of fluid between chambers and/or between a chamber and the environment, such as between second chamber 104 and an environment 130 outside the apparatus for treatment. As known in the art there are various types of airlocks. For example, the airlock type may be, for example, a front load air lock, a pass-through air lock, a rotary airlock, and combinations thereof. The airlock can comprise a housing, e.g., first chamber 102, having at least two airtight doors, opening 124 and passage 108, which can be operated one at a time (e.g., at any given time at least one door is closed). For example, in order to move the object 112 from the environment 130 into the second chamber 104, the opening 124 may be in the first state and the object is placed in the first position 128a within the first chamber 102. Then, the state of the opening 124 may be changed to the second state, such as a closed or sealed state, and thereafter the first passage 108 is configured into the first state, such as a open state. The object 112 is moved from the first position 128a to the second position 128b within the second chamber 104 via the first passage 108. The state of the first passage may be changed from the first state to the second state to limit movement of the object within the second chamber 104 for treatment. Accordingly, the first chamber 102 can minimize exchanges of a fluid, heat and pressure between the second chamber 104 and the environment 130 while enabling movement of the object 112 into and throughout the apparatus 100 for treatment.

The second chamber 104 can be configured to support the treatment process such as conducting the second treatment stage therein at a second pressure, a second temperature, and/or a second sterilant concentration. The second treatment stage can be any portion of the treatment process, such as, for example, the intake stage, the exposure stage, the exit stage, a subset thereof, and combinations thereof. The object 112 can be subjected to the second treatment stage including subjecting the object 112 to the second pressure, the second temperature, and/or the second sterilant concentration. In one example, the object 112 is in the second position 128b during the second treatment stage.

The object 112 can be returned to the first chamber 102 from the second chamber 104 utilizing the first passage 108. In one example, thereafter, the first chamber 102 can be configured to conduct a third treatment stage therein at a third pressure, a third temperature, and/or a third sterilant concentration. The third treatment stage can be any portion of the treatment process, such as, for example, the intake stage, the exposure stage, the exit stage, a subset thereof, and combinations thereof. The object 112 can be subjected to the third treatment stage including subjecting the object 112 to the third pressure, the third temperature, and/or the third sterilant concentration. In one example, the object 112 is in the first position 128a during the third treatment stage. Accordingly, the object 112 may enter and exit the treatment process utilizing the first chamber 102 to enable asynchronous addition/removal of objects from the second chamber 104.

Figure 2:
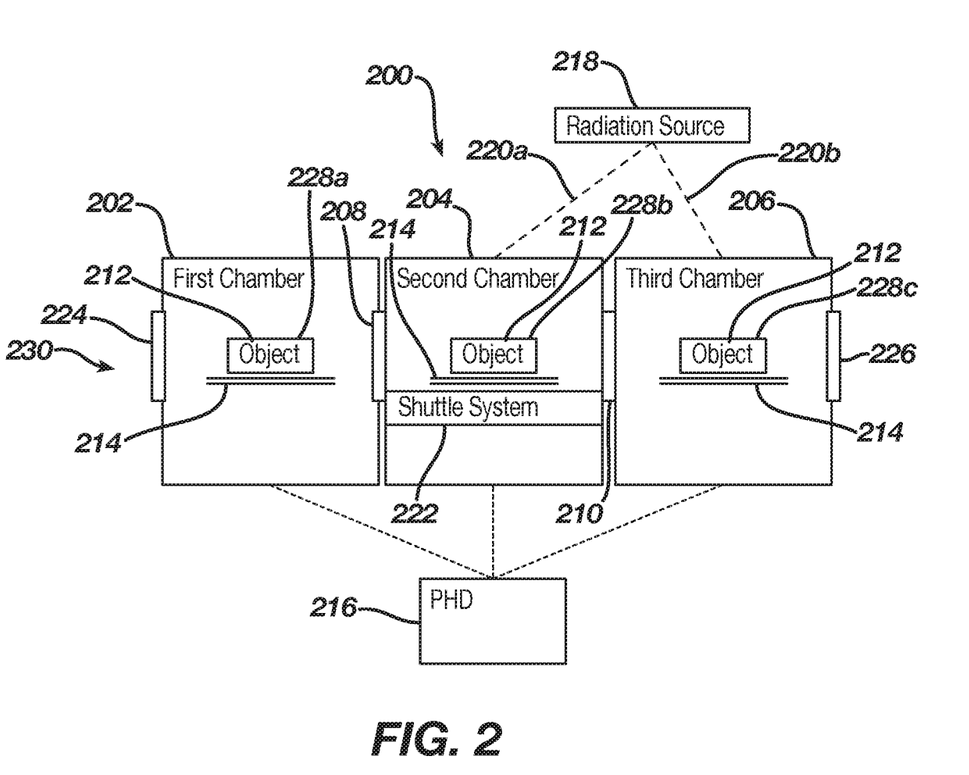
FIG. 2 is a block diagram illustrating a multi-chambered apparatus for treating an object.

FIG. 2 illustrates a multi-chambered apparatus 200 for treating an object 212. As shown, a first chamber 202 is configured with a first opening 224. The first opening 224 can be configured to receive an object 212 that is, or will be treated. The first opening 224 can have at least two states of communication, including a first state (e.g., an open state) which enables transport of the object 212 into/out of the first chamber 212 and a second state (e.g., a closed state, a sealed state, etc.) which limits transport of the object 212 into/out of the first chamber 202.

The first chamber 202 can be configured to support the treatment process such as conducting a first treatment stage therein at a first pressure, a first temperature, and/or a first sterilant concentration. The object 212 can be subjected to the first treatment stage including subjecting the object 212 to the first pressure, the first temperature, and/or the first sterilant concentration. In one example, during the first treatment stage the first opening 224 is in the second state. In one example, the object 212 is in a first position 228a within the first chamber 202 during the first treatment stage.

As shown, the first chamber 202 can be operatively coupled to a first passage 208 and a second chamber 204 can be operatively coupled to the first passage 208. The first passage 208 can facilitate communication between the first chamber 202 and the second chamber 204. For example, in one example, the first passage 208 has at least two states of communication, including a first state (e.g., an open state) which enables the first and second chambers, 202 and 204 respectively, to exchange at least one of: a fluid, heat, and pressure, and a second state (e.g., a closed state, a sealed state, etc.) which enables separation of the first and second chambers, 202 and 204 respectively. The first passage 208 can be configured to receive and/or facilitate transport of the object 212 from the first position 228a within the first chamber 202 to a second position 228b within the second chamber 204. In one example, the first chamber 102 is an airlock. In one example, during the first treatment stage and/or a second treatment stage, the first passage 108 is in the second state.

The second chamber 204 can be configured to support the treatment process such as conducting the second treatment stage therein at a second pressure, a second temperature, and/or a second sterilant concentration. The object 212 can be subjected to the second treatment stage including subjecting the object 212 to the second pressure, the second temperature, and/or the second sterilant concentration. In one example, the object 212 is in the second position 228b during the second treatment stage. In one example, at least one of the first pressure, the first temperature, and the first sterilant concentration is different from the second pressure, the second temperature, and the second sterilant concentration, respectively.

As shown, in one example, the second chamber 204 can be operatively coupled to a second passage 210 and a third chamber 206 can be operatively coupled to the second passage 210. The second passage 210 can facilitate communication between the second chamber 204 and the third chamber 206. For example, in one example, the second passage 210 has at least two states of communication, including a first state (e.g., an open state) which enables the second and third chambers, 204 and 206 respectively, to exchange at least one of: a fluid, heat, and pressure and a second state (e.g., a closed state, a sealed state, etc.) which enables separation of the second and third chambers, 204 and 206 respectively. The second passage 210 can be configured to receive and/or facilitate transport of the object 212 from the second position 228b to a third position 228c within the third chamber 206. In one example, the third chamber 206 is an airlock. In one example, during the second treatment stage and/or a third treatment stage, the second passage 208 is in the second state.

The third chamber 206 can be configured to support the treatment process such as conducting the third treatment stage therein at a third pressure, a third temperature, and/or a third sterilant concentration. The object 212 can be subjected to the third treatment stage including subjecting the object 212 to the third pressure, the third temperature, and/or the third sterilant concentration. In one example, the object 212 is in the third position 228c during the third treatment stage. In one example, at least one of the second pressure, the second temperature, and the second sterilant concentration is different from the third pressure, the third temperature, and the third sterilant concentration, respectively.

As shown, the third chamber 206 is configured with a second opening 226. The second opening 226 can be configured to receive the object 212. The second opening 226 can have at least two states of communication, including a first state (e.g., an open state) which enables transport of the object 212 into/out of the third chamber 206 and a second state (e.g., a closed state, a sealed state, etc.) which limits transport of the object 212 into/out of the third chamber 206. In one example, the second opening 226 is a sealable opening.

As shown, in one example, a radiation source 218 can be operatively coupled to the second chamber 204 and/or the third chamber 206 utilizing a first connection 220a and/or a second connection 220b, respectively. The first connection 220a and/or second connection 220b may be, for example, a direct connection, a wave guide, a surfaguide, and combinations thereof. The radiation source 218 may be one or more of a magnetron, a klystron, and a gyrotron. The radiation source 218 can be configured to generate radio frequency (RF) radiation, and/or microwave radiation, hereinafter referred to collectively as radiation, within the second chamber 204 and/or the third chamber 206 utilizing the first connection 220a and/or second connection 220b, respectively. A frequency(ies) of the radiation may be in the range of 60 hertz (Hz) to 300 gigahertz (GHz). For example, the frequency may be 60 Hz, in certain examples, the frequency may be 1 kilohertz (kHz), in another example, the frequency may be, 915 megahertz (MHz), and in yet another example, the frequency may be 2.45 GHz. In certain examples, the radiation may be a low frequency (LF) radiation. The radiation may generate a plasma within the respective chamber(s) before, during, and/or after the respective treatment stage. The generated plasma can, for example, activate the sterilant, remediate the sterilant within the respective chamber (e.g., degrade), heat the object 212, contributed to the treatment of object 212, and combinations thereof. In order to activate and/or remediate the sterilant, the plasma may physically change the sterilant. For example, if the sterilant is hydrogen peroxide, the plasma may remediate the sterilant by changing at least a portion of the hydrogen peroxide into water, and/or oxygen. In order to activate the sterilant, the plasma may physically change at least a portion of the hydrogen peroxide into a free radical and/or an active oxygen species. Accordingly, the radiation source 218 may support the second and/or third stages of the treatment process.

As shown, in one example, a shuttle system 222 may be in operative communication with the second chamber 204. The shuttle system 222 can be configured to transport the object 212 between the first chamber 202 and the second chamber 204, between the second chamber 204 and the third chamber 206, between the first chamber 202 and the environment 230, between the third chamber 206 and the environment 230, and combinations thereof. The shuttle system 222 may be any device which can facilitate movement of the object 212 such as, for example, a conveyor, a robotic transport vehicle, a manually actuated lever, a carousel, and combinations thereof. Accordingly, the shuttle system 222 facilitates movement of the object 212 between the chambers, 202-206.

In one example, the object 212 is physically supported in the first, second, and/or third position, 228a-c, and/or in an orientation by a support member 214 which may be, for example, a tray, a rack, a holder, a shelf, a container, and combinations thereof. In one example, the support member 214 may physically support multiple objects. The support member 214 may be moveable between positions, 228a-c, and/or removed from the chambers, 202-206 into the environment 230 outside of the apparatus for treatment. In one example, the support member 214 may be in a fixed position within the first, second, or third chambers 202, 204, and 206, respectively. In one example, multiple support members 214 may be present in any one of the chamber 202-206 at a time. Thus, the quantity of support members 214 shown is for illustration purposes only and should not be considered limiting. In one example, the shuttle system 222 is in communication with the support member 214 to facilitate movement of the support member 214 between positions 228a-c. Accordingly, the position and/or orientation of the object 212 can be physically supported by the support member 214.

As shown, in one example, one or more programmable hardware device (PHD) 216 can be provided with functionality to control a parameter of the treatment process. For example, the PHD may control a parameter of the first, second, and/or third treatment stages. The parameter may be, for example, the first pressure, the first temperature, the first sterilant concentration, the second pressure, the second temperature, the second sterilant concentration, the third pressure, the third temperature, the third sterilant concentration, a concentration of radiation within a respective chamber, a time the object spends in a respective chamber, and combinations thereof. In one example, the PHD 216 can be a hardware device configured with a processor operatively coupled to a memory. Accordingly, the PHD 216 can facilitate the treatment process by controlling the parameter.

The PHD 216 can control the time the object 212 spends in a respective chamber by utilizing the shuttle system 222 and/or changing the state of the first and/or second passage, 208 and 210 respectively, and/or changing the state of the first and second openings, 224 and 226 respectively. For example, in order to move the object 212 from the first position 228a to the second position 228b, the PHD may change the state of the first passage 208 to the first state and move the object 212 to the second position 228b from the first position 228a utilizing the shuttle system 222. Similarly, in order to move the object 212 from the second position 228b to the third position 228c, the PHD may change the state of the second passage 210 to the first state and move the object 212 to the third position 228c from the second positioned 228b utilizing the shuttle system 222. In order to remove the object 212 from the first and/or third chambers, 202 and 206 respectively, the PHD 216 may change the state of the first and/or second opening, 224 and 226 respectively, to the first state and remove the object 212 from the respective chamber utilizing the shuttle system 222. Accordingly, the PHD 216 can control the position of the object 212 utilizing the shuttle system 222.

The PHD 216 can control a temperature control unit (e.g., heater, cooler, etc.) associated with the chambers, 202, 204, and 206, in order to maintain and/or adjust a temperature within the respective chamber, such as the first, second, and/or third temperature. The PHD 216 can control a pressure source (e.g., pressure pump, vacuum pump, valve, etc.) associated with the first, second, and third chambers, 202, 204, and 206 respectively, in order to maintain and/or adjust a pressure within the respective chamber, such as the first pressure, the second pressure, and/or the third pressure. The PHD 216 can control a sterilant source (e.g., flow controller, pump, meter device, vaporizer, etc.) associated with the respective chamber in order to maintain and/or adjust a sterilant concentration within the respective chamber. The PHD 216 can control the radiation source 218 in order to maintain and/or adjust a radiation concentration with the respective chamber. Accordingly, the PHD 216 can automatically facilitate the treatment process with minimal, if any, intervention.

The PHD 216 may measure and/or record a process parameter of at least one of the chamber 202, 204, and 206 such as for example, a time, a temperature, a pressure, a sterilant concentration, and combinations thereof. The PHD 216 may dynamically adjust a second parameter of the treatment process based on the process parameter. For example, the PHD 216 can determine when to begin a treatment stage and/or move an object between chambers 202, 204, and 206 based on the process parameter. For example, when the process parameter meets or exceeds a threshold the PHD 216 may move the object 212 to a different chamber and/or begin a treatment stage. Accordingly, the PHD 216 may dynamically control the treatment process based on the process parameter.

In one example, the first treatment stage is the intake stage of the treatment process, the second treatment stage is the exposure stage of the treatment process, and the third treatment stage is the exit stage of the treatment process. In one example, the first treatment stage is the exit stage of the treatment process, the second treatment stage is the exposure stage of the treatment process, and the third treatment stage is the intake stage of the treatment process. In one example, the first treatment stage includes the intake and exposure stages of the treatment process and the second treatment stage includes the exit stage of the treatment process. In one example, the first treatment stage is the intake stage of the treatment process and the second treatment stage includes the exposure and exit stages of the treatment process. In one example, the first treatment stage includes a portion of the intake stage of the treatment process and the second treatment stage include a portion of the intake stage, and the exposure stage, and exit stage of the treatment process. Accordingly, the portion of the treatment process included in the first, second, and/or third treatment stages is for illustration purposes only and should not be considered limiting.

The chambers 202, 204, and 206 may conduct the first, second, and third treatment stages in sequence and/or concurrently or any combination thereof. For example, it is contemplated that two or more treatment processes may be conducted within the apparatus 200 at the same time. For example, a first object may be treated in the first treatment stage within the first chamber 202, a second object may be treated in the second treatment stage within the second chamber 204, and a third object may be treated in the third treatment stage within the third chamber 206, simultaneously. Similarly, less than all of the chambers 202, 204, and 206 (e.g., two of the chambers 202, 204, and 206, one of the chambers 202, 204, and 206, etc.) may be treating an object concurrently while a select chamber may not be treating an object. In one example, both the first and third chambers, 202 and 206, respectively, can conduct the first and third treatment stages therein and the second chamber 204 can conduct the second treatment stage therein.

Figure 3:
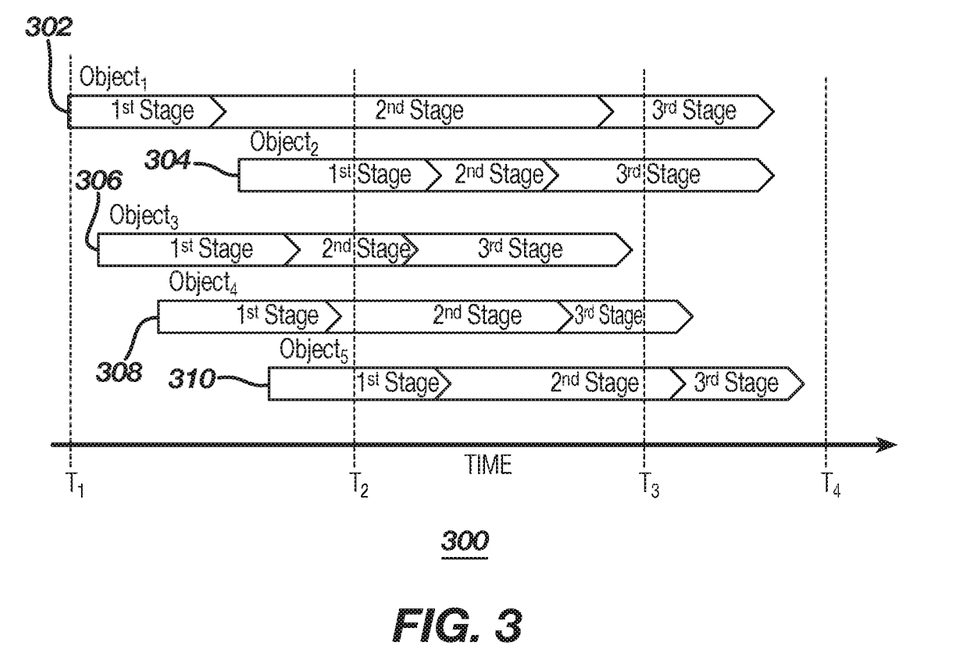
FIG. 3 is a chart illustrating an example of treatment processes of various objects over time.

The apparatus for treatment can dynamically accommodate multiple treatment processes such that the treatment processes can be tailored to efficiently and effectively treat dissimilar objects. The dynamic accommodation maximizes the level of sterilization for the objects while minimizing degradation and elapsed time to treat the objects. Referring to FIG. 3, a chart 300 is provided illustrating an example of treatment processes of various objects over time. As shown, $object_1$ is associated with a first treatment process 302; $object_2$ is associated with a second treatment process 304; $object_3$ is associated with a third treatment process 306; $object_4$ is associated with a fourth treatment process 308; and $object_5$ is associated with a fifth treatment process 310. The first treatment stage is at a first pressure, a first temperature, and a first sterilant concentration. Similarly, the second treatment stage is at a second pressure, a second temperature, and a second sterilant concentration; and the third treatment stage is at a third pressure, a third temperature, and a third sterilant concentration. In one example, the difference between the first, second, third, fourth, and fifth treatment processes, 302, 304, 306, 308, and 310, is an elapsed time of the respective treatment stages. Accordingly, the quantity of objects, the quantity, length, and start/stop time of treatment stages, the quantity, length, start/stop time of treatment processes is for illustration purposes only and should not be considered limiting.

As shown, at time, $T_1$, $object_1$ is being treated in the first treatment stage of the treatment process while $object_2$, $object_3$, $object_4$, and $object_5$ are not being treated in the treatment process. In one example, $object_1$ is positioned within the first chamber 202, and $object_2$, $object_3$, $object_4$, and $object_5$ are positioned in the environment 230 outside of the apparatus for treatment at time, $T_1$. In one example, $object_1$ is positioned within the third chamber 206 at time, $T_1$.

At time, $T_2$, $object_2$ and $object_5$ are being treated in the first treatment stage of the treatment process and $object_1$, $object_3$, and $object_4$ are being treated in the second treatment stage of the treatment process. In one example, $object_2$ and $object_5$ are positioned within the first chamber 202 and $object_1$, $object_3$, and $object_4$ are positioned within the second chamber 204 at time, $T_2$. In one example, $object_2$ and $object_5$ are positioned within the third chamber 206 at time, $T_2$.

At time, $T_3$, $object_5$ is being treated in the second treatment stage of the treatment process and $object_1$, $object_2$, and $object_4$ are being treated in the third treatment stage of the treatment process. $Object_3$ has completed its respective treatment process at time, $T_3$. In one example, $object_5$ is in the second chamber 204, $object_1$, $object_2$, and $object_4$ are in the third chamber 206, and $object_3$ has been removed from the treatment apparatus and placed into the environment 230 at time, $T_3$. In one example, $object_1$, $object_2$, and $object_4$ are in the first chamber 202 at time, $T_3$.

At time, $T_4$, $object_1$, $object_2$, $object_3$, $object_4$, and $object_5$ have completed their respective treatment process and in one example, have been removed from the treatment apparatus and placed into the environment 230. Thus, an object can be moved between chambers and/or treatment stages independently of another object. The independent movement can enable a treatment stage/process to be dynamically adjusted to a parameter of the respective object such as, for example, type, quantity, geometry, texture, material composition, soil level, and/or bioburden. Accordingly, an object can be independently moved throughout the treatment apparatus such that the accumulated lethality caused by a respective treatment process is maximized while minimizing degradation of the object.

Figure 4:
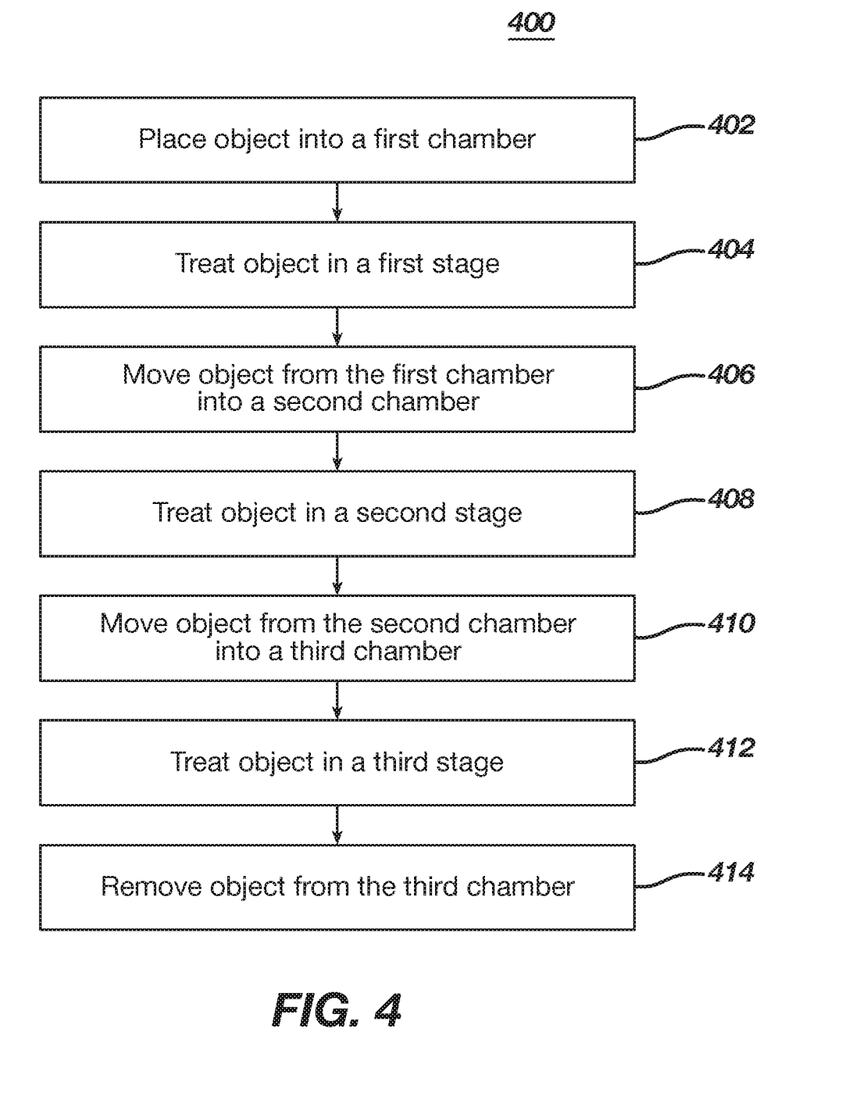
FIG. 4 is a flow chart illustrating a method for treating an object.

Referring to FIG. 4, a flow chart 400 is provided illustrating a method for treating an object. As shown, an object is placed into a first treatment chamber of an apparatus for treatment 402. In one example, the object is placed into the first treatment chamber via a first opening. The object is treated in a first treatment stage within the first treatment chamber at a first pressure, a first temperature, and/or a first sterilant concentration 404.

The object is moved from the first chamber into a second treatment chamber of the apparatus for treatment via the first passage 406. The object is treated in a second treatment stage within the second treatment chamber at a second pressure, a second temperature, and/or a second sterilant concentration 408. In one example, at least one of the first pressure, the first temperature, and the first sterilant concentration is different from the second pressure, the second temperature, and the second sterilant concentration, respectively. In one example, the second treatment stage remediates a portion of sterilant. In one example, the remediation includes generating radiation within the second chamber and generating a plasma.

In one example, the object is moved from the second treatment chamber into a third treatment chamber of the treatment apparatus via a second passage 410. The object is treated in a third treatment stage within the third treatment chamber at a third pressure, a third temperature, and/or a third sterilant concentration 412. In one example, the first and third treatment chambers can be the same chamber or different chambers. In one example, at least one of the second pressure, the second temperature, and the second sterilant concentration is different from the third pressure, the third temperature, and the third sterilant concentration, respectively. In one example, the second treatment stage remediates a portion of sterilant. In one example, the remediation includes generating radiation within the third chamber and generating a plasma. In one example, the object is removed from the third treatment chamber 414. In one example, when the object is removed from the treatment chamber, the object is in a substantially free of bacteria and/or other forms of living organisms.

In one example, a parameter of the first, second, and/or third treatment stages is controlled. The parameter may be, for example, the first temperature, the first pressure, the first sterilant concentration, the second temperature, the second pressure, the second sterilant concentration, the third temperature, the third pressure, the third sterilant concentration, and a concentration of radiation within the respective chamber. In one example, a time the object spends in the first chamber, second chamber, and/or third chamber is controlled. Accordingly, various parameters may be controlled throughout the treatment process.

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more examples has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various examples and with various modifications as are suited to the particular use contemplated. It is intended that the claims submitted herewith define the overall scope.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. An apparatus for treatment of an object, comprising:
    a first treatment chamber configured to conduct a first treatment stage therein comprising subjecting the object to a first pressure, a first temperature, and a first sterilant concentration;
    a first passage operatively connected to the first treatment chamber;
    a second treatment chamber operatively connected to the first passage and in communication with the first chamber via the first passage, the second chamber configured to conduct a second treatment stage therein comprising subjecting the object to a second pressure, a second temperature, and a second sterilant concentration;
    a hydrogen peroxide source associated with at least one of the first treatment chamber and the second treatment chamber, wherein the first sterilant concentration and the second sterilant concentration each comprise a hydrogen peroxide concentration; and
    a programmable hardware device in communication with the first chamber and the second chamber, the programmable hardware device configured to measure a first parameter selected from the group consisting of the first pressure, the first temperature, the first sterilant concentration, and a time the object spends in the first chamber; and, based on the measured first parameter, move the object to the second chamber, begin the second treatment stage, or a combination thereof.

2. The apparatus of claim 1, wherein at least one of the first pressure, the first temperature, and the first sterilant concentration is different from the second pressure, the second temperature, and the second sterilant concentration, respectively.

3. The apparatus of claim 1, further comprising:
a second passage, wherein the second chamber is operatively connected to the second passage; and
a third treatment chamber operatively connected to the second passage and in communication with the second chamber via the second passage, the third chamber configured to conduct a third treatment stage therein at a third pressure, a third temperature, and a third sterilant concentration.

4. The apparatus of claim 3, wherein at least one of the second treatment stage and the third treatment stage remediates a portion of sterilant comprising hydrogen peroxide.

5. The apparatus of claim 4, further comprising a radiation source operatively connected to at least one of the second chamber and the third chamber, the radiation source configured to generate a plasma therein, wherein the plasma is utilized for remediation of the portion of the sterilant.

6. The apparatus of claim 3, further comprising:
a first opening in the first chamber, the first opening configured to receive the object into the first chamber;
the first passage configured to facilitate transport of the object between the first chamber and the second chamber;
the second passage configured to facilitate transport of the object between the second chamber and the third chamber; and
a second opening in the third chamber, the second opening configured to facilitate transport of the object out of the third chamber.

7. The apparatus of claim 1, wherein the first treatment chamber comprises an airlock.

8. The apparatus of claim 1, wherein the programmable hardware device is configured to control a parameter in at least one of the first treatment stage and the second treatment stage.

9. The apparatus of claim 8, wherein the parameter is selected from the group consisting of the first temperature, the first pressure, the first sterilant concentration, the second temperature, the second pressure, the second sterilant concentration, and combinations thereof.

10. The apparatus of claim 1, wherein the programmable hardware device is configured to control a time the object spends in at least one of the first chamber and the second chamber.

11. The apparatus of claim 1, further comprising:
a shuttle system in communication with the second chamber, the shuttle system configured to transport the object between the first chamber and the second chamber.

12. The apparatus of claim 1, wherein the first passage has at least two states of communication, including a first state which enables the first and second chambers to exchange at least one of: a fluid, heat, and pressure and a second state which enables separation of the first and second chambers.

13. An apparatus for treatment of a medical device, comprising:
a first treatment chamber configured to conduct a first treatment stage therein comprising subjecting the medical device to a first pressure, a first temperature, and a first sterilant concentration;
a second treatment chamber operatively connected to the first passage and in communication with the first chamber via the first passage, the second treatment chamber configured to conduct a second treatment stage therein comprising subjecting the medical device to a second pressure, a second temperature, and a second sterilant concentration that is different from at least one of the first pressure, the first temperature, and the first sterilant concentration, respectively;
a shuttle system in communication with the second chamber, the shuttle system configured to transport the medical device between the first chamber and the second chamber via the first passage;
a programmable hardware device configured to control a parameter in at least one of the first treatment stage and the second treatment stage, wherein the parameter is selected from the group consisting of the first pressure, the first temperature, the first sterilant concentration, the second pressure, the second temperature, the second sterilant concentration, a time the medical device spends in at least one of the first chamber and the second chamber, and combinations thereof, wherein the programmable hardware device is configured to, based on the parameter, move the object to the second chamber, begin the second treatment stage, or a combination thereof; and
a hydrogen peroxide source associated with at least one of the first treatment chamber and the second treatment chamber, wherein the first sterilant concentration and the second sterilant concentration each comprise a hydrogen peroxide concentration.

14. The apparatus of claim 1, wherein the first passage is moveable along a path from a first location to a second location, wherein a movement of the object between the first chamber and the second chamber is not impeded by the first passage in the first location and is impeded by the first passage in the second location.

15. The apparatus of claim 14, wherein the first passage is configured to create a seal between the first chamber and the second chamber in the second location.

16. The apparatus of claim 1, further comprising a support member configured to physically support the object in at least one of the first chamber and the second chamber.

17. The apparatus of claim 1, wherein the first chamber is configured to conduct the first treatment stage concurrently while the second chamber conducts the second treatment stage.

18. The apparatus of claim 3, wherein the first chamber is configured to establish a treatment condition, the second chamber is configured to maintain and/or adjust the treatment condition, and the third chamber is configured to remove the treatment condition.

19. The apparatus of claim 6, wherein at least one of the first opening and the second opening is a sealable opening.

20. The apparatus of claim 1, wherein at least one of the first sterilant concentration and the second sterilant concentration comprise a hydrogen peroxide concentration greater than 1% hydrogen peroxide vapor by weight.

21. The apparatus of claim 13, wherein at least one of the first sterilant concentration and the second sterilant concentration comprise a hydrogen peroxide concentration greater than 1% hydrogen peroxide vapor by weight.

* * * * *